US012102438B2

(12) United States Patent
Balda et al.

(10) Patent No.: US 12,102,438 B2
(45) Date of Patent: Oct. 1, 2024

(54) PENDANT PHYSIOLOGICAL SIGNAL MONITOR AND ASSOCIATED SYSTEMS AND METHODS

(71) Applicant: Medicomp, Inc., Melbourne, FL (US)

(72) Inventors: Anthony Balda, Satellite Beach, FL (US); George Koos, Melbourne Beach, FL (US)

(73) Assignee: Medicomp, Inc., Melbourne, FL (US)

( * ) Notice: Subject to any disclaimer, the term of this patent is extended or adjusted under 35 U.S.C. 154(b) by 144 days.

(21) Appl. No.: 15/692,639

(22) Filed: Aug. 31, 2017

(65) Prior Publication Data

US 2019/0059757 A1 Feb. 28, 2019

(51) Int. Cl.
*A61B 5/00* (2006.01)
*A61B 5/0205* (2006.01)
(Continued)

(52) U.S. Cl.
CPC ............ *A61B 5/332* (2021.01); *A61B 5/0022* (2013.01); *A61B 5/02055* (2013.01); *A61B 5/02438* (2013.01); *A61B 5/0816* (2013.01); *A61B 5/1116* (2013.01); *A61B 5/14551* (2013.01); *A61B 5/291* (2021.01); *A61B 5/296* (2021.01);
(Continued)

(58) Field of Classification Search
CPC ............ A61B 5/04085; A61B 5/04087; A61B 5/6814; A61B 5/6822; A61B 5/6823; A61B 5/6826; A61B 5/6831; A61M 5/14248
See application file for complete search history.

(56) References Cited

U.S. PATENT DOCUMENTS 6,605,046 B1 * 8/2003 Del Mar ............ A61B 5/04085
600/507
7,257,438 B2 * 8/2007 Kinast .................. A61B 5/0402
600/301

(Continued)

FOREIGN PATENT DOCUMENTS

WO 9959465 A1 11/1999
WO 2004008954 A1 1/2004

OTHER PUBLICATIONS

Extended European Search Report dated Oct. 29, 2018; 8 pages.

*Primary Examiner* — Sana Sahand
(74) *Attorney, Agent, or Firm* — Kelly G. Swartz; Widerman Malek, PL

(57) ABSTRACT

A physiological signal monitoring system comprising a pendant and a patch. The pendant includes a data store, a processor, and a cellular modem. The patch includes a cradle and electrodes mechanically and electrically connected with a flexible printed circuit board (PCB). When removably coupled with the cradle of the patch, the pendant receives from the electrodes electrical signals from a patient's heart and either stores the signals to the data store or transmits the signals. A single channel patch configuration includes two electrodes positioned at least 8.0 centimeters (CM) apart. A two channel patch configuration employs three electrodes similarly spaced. Removable auxiliary components may connect to the pendant's device interfaces, each configured to receive physiological input such as electromyogram (EMG), electroencephalogram (EEG), body temperature, heart rate, pedometer, blood pressure, pulse oximetry, respiratory rate, posture/body orientation, and sleep monitoring.

19 Claims, 11 Drawing Sheets

(51) Int. Cl.
| | |
|---|---|
| *A61B 5/024* | (2006.01) |
| *A61B 5/08* | (2006.01) |
| *A61B 5/11* | (2006.01) |
| *A61B 5/1455* | (2006.01) |
| *A61B 5/291* | (2021.01) |
| *A61B 5/296* | (2021.01) |
| *A61B 5/30* | (2021.01) |
| *A61B 5/332* | (2021.01) |
| *A61B 5/021* | (2006.01) |
| *A61B 5/259* | (2021.01) |
| *A61B 5/282* | (2021.01) |
| *A61B 5/333* | (2021.01) |

(52) U.S. Cl.
CPC ............ *A61B 5/303* (2021.01); *A61B 5/4561* (2013.01); *A61B 5/4806* (2013.01); *A61B 5/6822* (2013.01); *A61B 5/6823* (2013.01); *A61B 5/6826* (2013.01); *A61B 5/7475* (2013.01); *A61B 5/021* (2013.01); *A61B 5/112* (2013.01); *A61B 5/259* (2021.01); *A61B 5/282* (2021.01); *A61B 5/333* (2021.01); *A61B 2560/0443* (2013.01); *A61B 2562/0209* (2013.01); *A61B 2562/164* (2013.01); *A61B 2562/166* (2013.01)

(56) References Cited

U.S. PATENT DOCUMENTS

| | | | |
|---|---|---|---|
| 7,382,247 B2 | 6/2008 | Welch et al. | |
| 8,147,446 B2* | 4/2012 | Yodfat | A61M 5/14248 604/131 |
| 9,241,635 B2 | 1/2016 | Yuen et al. | |
| 2008/0097231 A1* | 4/2008 | Balda | A61B 5/02438 600/509 |
| 2008/0108890 A1* | 5/2008 | Teng | A61B 5/259 600/372 |
| 2008/0281168 A1* | 11/2008 | Gibson | A61B 5/002 600/301 |
| 2008/0288026 A1* | 11/2008 | Cross | A61B 5/6833 607/60 |
| 2009/0076363 A1* | 3/2009 | Bly | A61B 5/0464 600/372 |
| 2010/0081913 A1* | 4/2010 | Cross | A61B 5/282 600/509 |
| 2010/0292595 A1* | 11/2010 | Paul | A61B 5/332 600/509 |
| 2011/0021937 A1* | 1/2011 | Hugh | A61B 5/0006 600/523 |
| 2011/0266999 A1* | 11/2011 | Yodfat | A61M 5/1413 320/107 |
| 2012/0088999 A1* | 4/2012 | Bishay | A61B 5/332 600/382 |
| 2013/0116533 A1* | 5/2013 | Lian | A61B 5/0006 600/391 |
| 2013/0307685 A1* | 11/2013 | Sholder | G08B 21/02 340/539.12 |
| 2013/0345578 A1* | 12/2013 | Nadkarni | G01P 1/12 600/509 |
| 2014/0051946 A1* | 2/2014 | Arne | A61B 5/0006 600/301 |
| 2014/0180029 A1* | 6/2014 | Hansmann | A61B 5/113 600/301 |
| 2014/0187974 A1* | 7/2014 | Banet | A61B 5/6822 600/483 |
| 2014/0275928 A1 | 9/2014 | Acquista et al. | |
| 2015/0087950 A1* | 3/2015 | Felix | A61B 5/335 600/382 |
| 2015/0087951 A1* | 3/2015 | Felix | A61B 5/04085 600/382 |
| 2015/0094559 A1* | 4/2015 | Russell | A61B 5/6833 600/391 |
| 2015/0150505 A1* | 6/2015 | Kaskoun | A61B 5/6833 600/300 |
| 2015/0150506 A1* | 6/2015 | Woo | A61B 5/0002 600/391 |
| 2015/0297134 A1 | 10/2015 | Albert et al. | |
| 2016/0113535 A1* | 4/2016 | Marek | A61B 5/0006 600/384 |
| 2016/0120433 A1* | 5/2016 | Hughes | A61B 5/6832 600/483 |
| 2016/0296132 A1* | 10/2016 | Bojovic | A61B 5/04012 |
| 2016/0374583 A1* | 12/2016 | Cerruti | A61B 5/0006 600/301 |
| 2019/0320984 A1* | 10/2019 | Elliott | G01K 13/002 |

\* cited by examiner

PENDANT PHYSIOLOGICAL SIGNAL MONITOR AND ASSOCIATED SYSTEMS AND METHODS

RELATED APPLICATIONS

This application claims the benefit under 35 U.S.C. § 119(a)-(d) of International Publication Number WO 2016/168315 filed on Apr. 13, 2016 and titled Pendent Physiological Signal Monitor and Associated System and Methods, which claims the benefit under 35 U.S.C. § 119(e) of U.S. Provisional Patent Application Ser. No. 62/146,740 filed by the inventor of the present application on Apr. 13, 2015, and titled Pendant Physiological Signal Monitor and Associated System and Methods, the entire content of which is incorporated herein by reference except to the extent that disclosure therein is inconsistent with disclosure herein.

This application is related to U.S. Pat. No. 9,498,145, titled Cardiac Event Monitoring System filed by the inventor of the present application on Jul. 22, 2014 which, in turn, is a continuation and claims the benefit under 35 U.S.C. § 120 of U.S. Pat. No. 9,198,590, titled Cardiac Event Monitoring System filed by the inventor of the present application on Mar. 5, 2014, which, in turn, is a continuation and claims the benefit under 35 U.S.C. § 120 of U.S. Pat. No. 8,983,583, titled Cardiac Event Monitoring System filed by the inventor of the present application on Oct. 18, 2006, the entire contents of each of which are incorporated herein by reference except to the extent that disclosure therein is inconsistent with disclosure herein.

This application is also related to U.S. Pat. No. 8,954,137, titled Use of Patterns in Processing on Mobile Monitoring Device and Computer System filed by the inventor of the present application on Jun. 18, 2012 which, in turn, is a continuation and claims the benefit under 35 U.S.C. § 120 of U.S. Pat. No. 8,204,580, titled Use of Patterns in Processing on Mobile Monitoring Device and Computer System, filed May 24, 2005 by the inventor of the present application, and which, in turn, claims the benefit under 35 U.S.C. § 119(e) of U.S. Provisional Patent Application Ser. No. 60/574,268, titled Wireless ECG Mobile Device That Communicates With A Base Station, filed by the inventor of the present application on May 25, 2004, the entire contents of each of which are incorporated herein by reference except to the extent that disclosure therein is inconsistent with disclosure herein.

This application is further related to U.S. Pat. No. 8,983,587 titled Cooperative Processing with Mobile Monitoring Device and Computer System filed on Jun. 4, 2013 which is a continuation-in-part of U.S. Pat. No. 8,483,807 titled Cooperative Processing with Mobile Monitoring Device and Computer System filed on May 11, 2010, which is a continuation of U.S. Pat. No. 7,715,905, titled Cooperative Processing with Mobile Monitoring Device and Computer System filed on May 24, 2005, which claims the benefit of U.S. Provisional Patent Application Ser. No. 60/574,268 filed May 25, 2004 and titled Wireless ECG Mobile Device that Communicates with a Base Station, the contents of which are incorporated in their entirety herein except to the extent that disclosure therein is inconsistent with disclosure herein.

This application is still further related to U.S. Pat. No. 9,131,867, titled Atrial Fibrillation Detection filed by the inventor of the present application on Apr. 22, 2013 which, in turn, is a continuation and claims the benefit under 35 U.S.C. § 120 of U.S. Pat. No. 8,428,705, titled Atrial Fibrillation Detection filed Sep. 22, 2009, and which, in turn, is a continuation and claims the benefit under 35 U.S.C. § 120 of U.S. Pat. No. 7,596,405, titled Atrial Fibrillation Detection filed Mar. 7, 2005, the contents of which are incorporated in their entirety herein except to the extent that disclosure therein is inconsistent with disclosure herein.

FIELD OF THE INVENTION

The present invention relates generally to systems and methods for medical monitoring of physiological signals and parameters and, more particularly, to wearable devices with integrated ECG sensors for ambulatory ECG monitoring, and related systems and methods.

BACKGROUND

Heart disease is a leading cause of death in the United States. Some patients may benefit from long-term ECG monitoring outside of a clinical setting. For example, atrial fibrillation and myocardial ischemia may occur episodically. Some episodes may occur without patient symptoms. Myocardial ischemia, if persistent and serious, can lead to myocardial infarction (heart attack). During a myocardial infarction, electrophysiological changes may be detected by an ECG monitoring device. For accurate diagnosis and effective treatment of many episodic heart conditions, medical professionals need to receive accurate and timely information regarding the frequency and duration of such episodes.

In conventional long-term ECG monitoring, such as with continuous Holter monitors or event monitors, mounting of the monitor typically involves preparation of the patient's skin to receive the monitoring device. Chest hair may be shaved or clipped from men. The skin is abraded to remove dead skin cells, and cleaned. A technician trained in electrode placement applies the electrodes to the skin with an adhesive. Each electrode of such conventional monitors is attached to an insulated wire that is routed some distance across the patient's body to an amplifier designed to amplify the ECG signal in preparation for further processing. Such monitoring systems are often worn by a patient for up to a month.

Traditional long-term monitoring systems like those described above present a number of problems. For example, abrading in preparation for electrode mounting often leaves the patient's skin irritated. During use, the patient must be careful not to pull on the wires connected to the electrodes, lest the electrodes be pulled off the skin. Removing an electrode with its strong adhesive may be painful to the patient. Furthermore, certain types of electrodes require use of a gel next to the skin to improve conductivity at the point of connection of the metal electrode to the skin. Prolonged exposure to the gel can irritate the skin. These and other discomfort factors associated with traditional long-term monitoring solutions may discourage a patient from using the ECG monitor as directed by medical personnel.

Alternative health monitoring system designs exist that attempt to address the many shortcomings of traditional ECG monitors. For example, some monitor implementations known in the art are based on an article of apparel designed to be conveniently and comfortably worn by the patient, such as a wrist band or finger ring. Also for example, some monitors are implemented as earphones equipped with sensors and data communications means. However, the still-prominent profile of such monitors still may make wear of the devices uncomfortable and use of such devices errorprone. Furthermore, currently available types of medical/health monitoring solutions typically require separate devices for monitoring different physiological parameters. At best, some existing devices are capable of limited simultaneous monitoring or interchangeability.

U.S. Patent Application Publication No. 2014/0243612 by Li et al. discloses a portable handheld device for simultaneously monitoring pulse waveforms indicative of blood pressure, blood oxygen levels, and electrocardiogram (ECG) signals. Data from the device may be analyzed onboard, with local computerized devices, and with remote server based systems. However, this multifunctioning handheld device does not support interchangeability of the various types of monitoring components.

U.S. Patent Application Publication No. 2012/0259233 by Chan et al. discloses a wireless method for using at least one "cloud" server to remotely monitor the physiological status of an ambulatory patient, including the patient's heart rate, heart rhythm morphology, breathing, and blood pressure. Data from the device may be analyzed onboard, with local computerized devices, and/or with remote server based systems. However, like the Li implementation described above, this multifunctioning remote monitor does not support interchangeability of the various types of monitoring components.

No device currently exists that supports seamless interchangeability between multiple monitoring types. Consequently, a need exists for increasingly comfortable and convenient monitoring devices for both personal and medical use, and that overcome the shortcomings of common implementations in the field.

For definition purposes, known techniques for signal gathering from the heart may be useful in understanding design of the present invention. Referring now to FIGS. 5A, 5B, and 5C, ECG signals gathered of the human heart may be represented as standardized vectors. Two types of vectors that may be taken into account when using conductors to measure ECG signals include the limb leads and the chest leads. The limb leads may be deployed about a front plane of a patient's body, as exemplified in FIG. 5A. The chest leads may monitor vectors in a transversal plane of the heart (e.g., deployed about a trunk of the patient's body as if viewed from above), as exemplified in FIG. 5B. Each of these lead types may generate a clear output that may contain information about the patient's heart's electrical impulses. FIG. 5C is a graph illustrating sample output of both limb and chest leads. Known, commercially-available ECG monitoring products make use of the vectors Lead I and Lead II for limb leads and V1 and V2 for chest leads.

While certain aspects of conventional technologies have been discussed to facilitate disclosure of the invention, the applicant in no way disclaims these technical aspects, and it is contemplated that the claimed invention may encompass one or more of the conventional technical aspects discussed herein. The present invention may address one or more of the problems and deficiencies of the current availability and prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein, or limited to the particular embodiment for the invention used to illustrate the steps and functionality of the herein.

This background information is provided to reveal information believed by the applicant to be of possible relevance to the present invention. No admission is necessarily intended, nor should be construed, that any of the preceding information constitutes prior art against the present invention. This reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

With the foregoing in mind, embodiments of the present invention are related to systems and methods for monitoring a health status of a patient using a monitoring system. The present invention may comprise a patient worn ECG device that may record and wirelessly communicate critical heart beat information to be processed by the client so as to advantageously provide users with a more efficient way of monitoring an effectively endless variety of physiological parameters. Systems and methods such as the one proposed herein may advantageously reduce cost dramatically, allowing a greater number of people to acquire and access medically relevant information about themselves. Systems and methods such as the one proposed herein may advantageously provide a great deal of convenience and versatility compared to the technology that currently exists. Systems and methods such as the one proposed herein may advantageously provide an efficient and cost-effective means of versatile monitoring and could potentially incorporate a variety of different monitoring capabilities.

More specifically, the present invention may include a physiological signal monitoring system comprising a pendant and a patch. The pendant may include a data store and a processor. The patch may include a cradle and electrodes configured in electrical communication with a flexible printed circuit board (PCB). The pendant may removably couple with the cradle of the patch.

The pendant may include a cellular modem. The pendant may include a recording activation button.

The pendant may receive from the electrodes electrical signals from a heart of a patient. The processor of the pendant may operate to store the electrical signals as ECG data to the data store. A single channel configuration of the patch may include two electrodes (a Right Arm RA electrode and a Left Leg LL electrode) positioned at least 8.0 centimeters (CM) apart. A two channel configuration of the patch may add a third electrode (a Left Arm LA electrode) such that the LA electrode and the LL electrode are similarly positioned at least 8.0 CM apart.

The pendant may be characterized by some number of device interfaces, each configured to receive signal communication from at least one removable auxiliary component configured to convey at least one of the following types of physiological input: electromyogram (EMG), electroencephalogram (EEG), body temperature, heart rate, pedometer, blood pressure, pulse oximetry, respiratory rate, posture/body orientation, and sleep monitoring.

A method aspect of the present invention may include the steps of providing the patch and pendant components as described above, determining that the pendant is removably coupled to the cradle of the patch, operating the processor of the pendant to receive the electrical signals and/or physiological input as described above, and operating a cellular modem to transmit the physiological input to at least one of a cellular network access point and a base station.

DETAILED DESCRIPTION OF THE INVENTION

Figure 1:
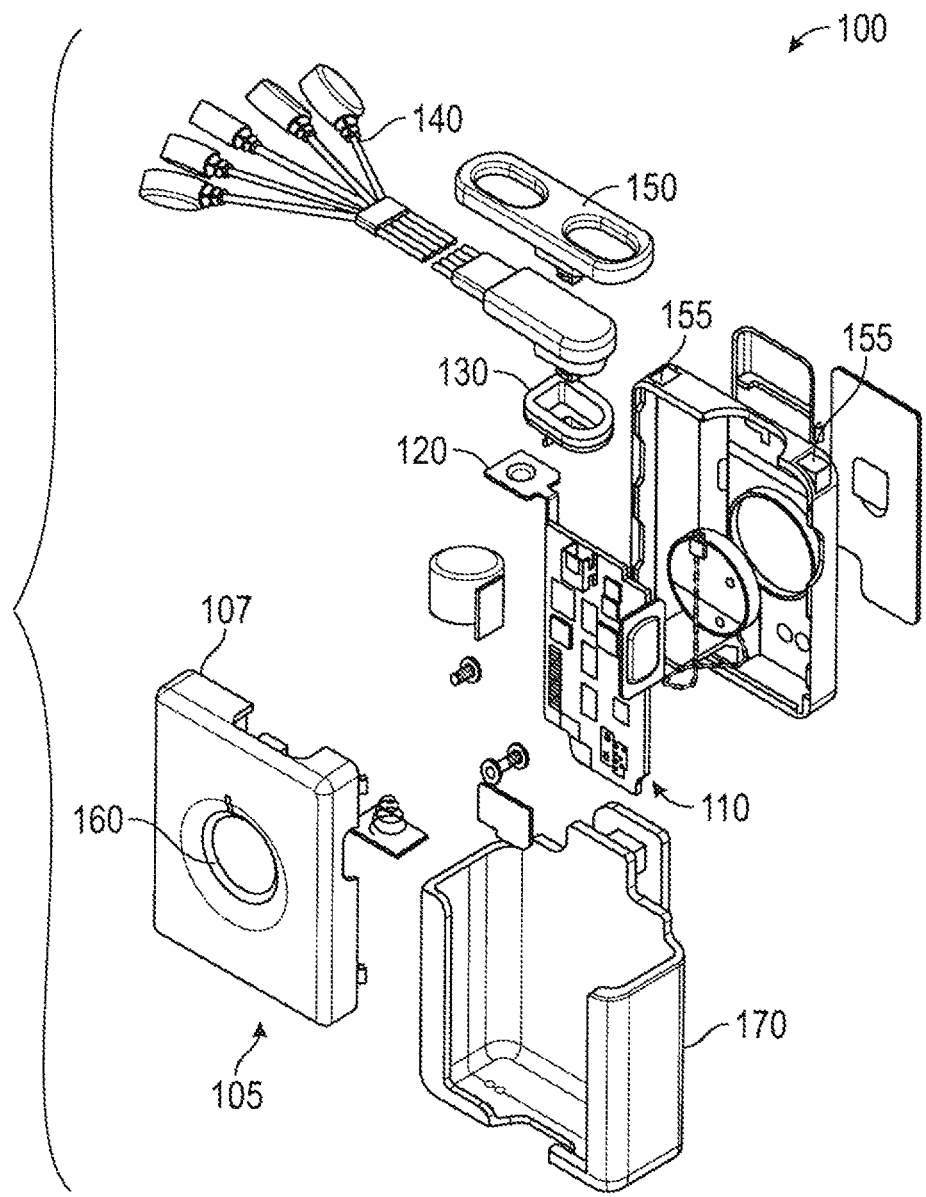
FIG. 1 is an exploded view of a pendant component and exemplary accessories of a pendant physiological signal monitor according to an embodiment of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Throughout this disclosure, the present invention may be referred to as a pendant physiological signal monitoring system, a patch monitor system, a patch monitor, a patch system, a patch pendant, a patch device, a multi-purpose patch monitor, a patch heartrate monitor, a patch, a monitor, a computer program product, a computer program, a product, a system, a device, and a method. Furthermore, the present invention may be referred to as relating to generally to physiological condition monitoring. Those skilled in the art will appreciate that this terminology does not affect the scope of the invention.

Example methods and systems for a pendant physiological signal monitor, and associated systems and methods, are described herein below. In the following description, for purposes of explanation, numerous specific details are set forth to provide a thorough understanding of example embodiments. It will be evident, however, to one of ordinary skill in the art that the present invention may be practiced without these specific details and/or with different combinations of the details than are given here. Thus, specific embodiments are given for the purpose of simplified explanation and not limitation.

An embodiment of the invention, as shown and described by the various figures and accompanying text, provides a device, system, and/or method capable of advantageously harvesting and monitoring a plurality of physiological signals. This device may be used in a formal medical setting (medically prescribed form), or as an over-the-counter (OTC) device available for commercial sale to the public for those interested in general health and fitness.

An embodiment of a physiological signal monitoring system may comprise two main components: a first component, hereinafter referred to as a pendant, comprising electrical elements that may be encased by a housing; and a second component, hereinafter referred to as a carrier, comprising a cradle to which the pendant may be configured to removably attach. A person of ordinary skill in the art would recognize that the pendant disclosed herein may be deployed in combination with a variety of physically and electrically compatible carrier designs (as exemplified below).

Figure 2:
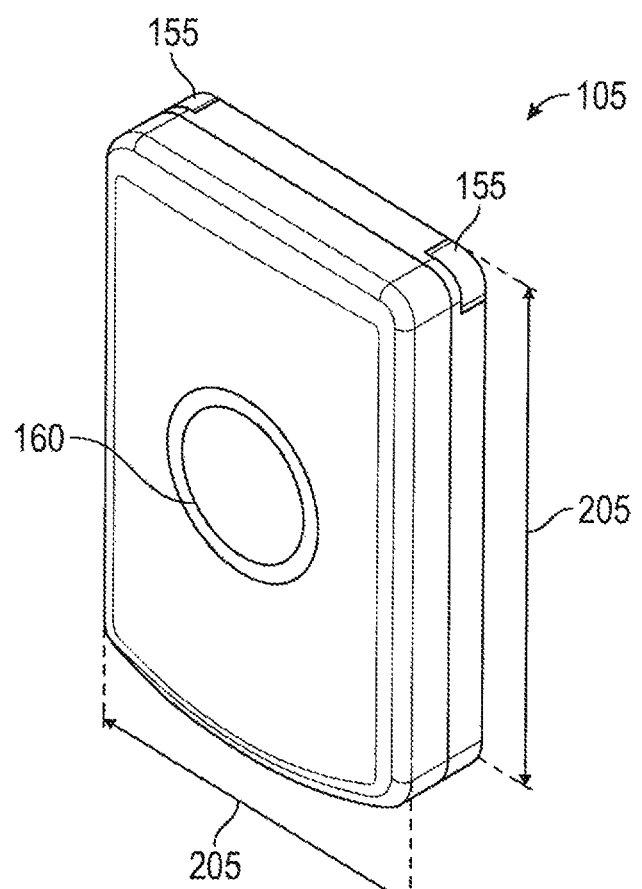
FIG. 2 is a perspective assembled view of a pendant component of a pendant physiological signal monitor according to an embodiment of the present invention.

Referring now to FIGS. 1 and 2, according to one embodiment of the present invention, a pendant 105 may advantageously feature a water resistant housing 107 characterized by an overall size 205 that may be approximately 60% smaller than the size of ECG monitoring system solutions currently known in the art. For example, and without limitation, such size reduction compared systems that feature a separate transmitter board, as known in the art, may be made possible by use of a single system on a chip (SoC) 110 capable of executing programmable functions, including performing wireless communication via an integrated antenna 120. For example, and without limitation, the pendant 105 may comprise a variety of device interfaces 130 that may facilitate interchangeable connectivity with the carrier component, such as, for example, and without limitation, a patch (as described hereinbelow), and also various accessory devices, such as, for example, and without limitation, a cable harness 140 (e.g., for a 3-wire cable or a 5-wire cable), a retractable monitor device, and/or a finger electrode adapter 150.

Other features of the pendant 105, according to various embodiments of the present invention, may include one or more of the following electrical elements:

recording activation button 160,
data storage 340 (for example, and without limitation, 30-day storage capacity of approximately 2.75 Gbyte,
data ports to support two or more communication channels, and/or
connection port for IBM-compatible PC or MAC.

The electrical elements of the pendant 105 may be configured to deliver overall device functionality. For example, and without limitation, the pendant 105 may be configured to carry circuitry necessary to advantageously perform biosignal harvest, evaluation, and intercommunication activities. Also for example, and without limitation, the electrical elements of the pendant 105 may have the ability to harvest, record, and/or analyze some number or types of input data channels at a given instance in time. Also for example, and without limitation, the electrical elements of the pendant 105 may be configured to perform data extraction, system updates, and other data manipulation capacities via wireless data transmission (e.g., cellular network communication, BlueTooth, Zigbee, WiFi) and/or via wired connection (e.g., USB, microUSB) to computing equipment external to the device. The pendant 105 may also comprise a user interface (for example, and without limitation, one or more of integrated fingertip ECG electrodes 155, liquid crystal display (LCD), touch-screen display, indicator lights, power switch/button, and recording activation button 160).

Figure 3:
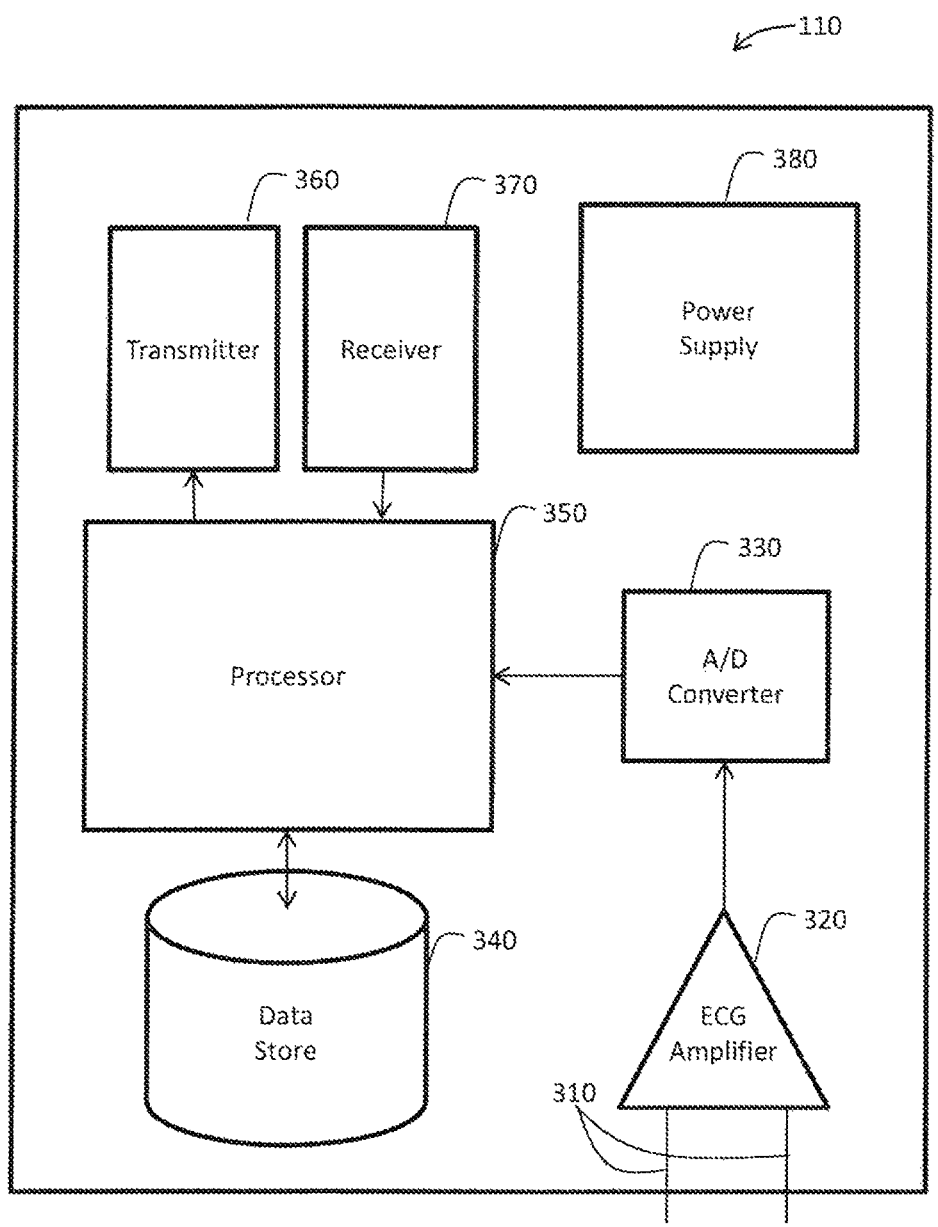
FIG. 3 is a schematic block diagram of a system on a chip (SoC) as implemented in a pendant component of pendant physiological signal monitor according to an embodiment of the present invention.

Referring now to FIG. 3, and continuing to refer to FIG. 1, the SoC 110 typically may include at least one input connector 310 that may be connected to a signal amplifier 320. The amplifier 320 may come into electrical contact with a conductor of an ECG lead. For example, and without limitation, the amplifier 320 may receive signals from the conductor via an integrated wiring system. The signals from the conductor may be amplified and subsequently converted by an A/D converter 330. For example, and without limitation, the A/D converter 330 may be configured to digitize the signals from the amplifier 320, and may optionally include filters to filter the signals or perform signal processing and identification of physiological conditions. The amplified and converted signals may be directed into processing and storage circuitry that may include a data store 340 and a processor 350 to implement filtering and processing functions to provide intermediate results and to store information before transmission to computing resources or monitoring personnel outside of the pendant 105. For example, and without limitation, filtering and processing functions employed on computing resources either local to the SoC 110 or remote from the pendant 105 may be configured to execute algorithms as described by the related applications incorporated by reference herein. In one such embodiment, the pre-processing circuitry of the SoC 110 may electrically couple the processed signals to a transmitter 360 (which may include the integrated antenna 120) that may transmit the signals to a base station (not shown) and/or directly to a cellular network. The signals may be transmitted using, for example, Zigbee, cellular, or Bluetooth protocols, to a base station that may be a computer, personal data assistant (PDA), cell tower, or smartphone. Other circuitry (not shown) may include timing and interface circuitry. In one embodiment, the components comprising the SoC 110, or portions of the SoC 110 may be discrete hardware components.

As related above, the electrical conductor selected may be in data communication with the data store 340, which may retain recorded signals until transmitted (transient) and/or may retain recorded signals until either manually or automatically deleted (persistent). The transmitter 360 may be configured to receive data from at least one of the conductor and the data store 340, and to communicate the data representing electrical signals detected by the conductor. Also for example, and without limitation, the housing 107 may carry a receiver 370 that may be configured in electrical communication with the data store 340. The receiver 370 may be configured to receive data and route those data to the data store 340 through the processor 350. For example, and without limitation, both communication of data from the transmitter 360 and receipt of data by the receiver 370 may occur wirelessly using the integrated antenna 120 and/or over wired connection. In one embodiment of wireless communication, the transmitter 360 and/or the receiver 370 may be implemented using radio frequency identification (RFID) or cellular technology.

In one embodiment, the pendant 105 may function as a stand-alone monitoring unit when the pendant 105 is configured in electrical communication with a contact electrode system. For example, and without limitation, a cable harness 140 may be positioned outside of the pendant 105 in such a manner that the electrode elements of the cable harness 140 may be exposed and readily accessible by the user. These electrodes may be placed on the body of the user in such a way that the contacts may be in position to harvest the desired physiological signal. Placement of the electrodes may be accomplished by the user herself and/or by another individual. In another embodiment, the pendant 105 may function as a stand-alone monitoring unit when the pendant 105 is configured in electrical communication with integrated fingertip ECG electrodes 155 and/or a fingertip electrode adapter 150. So configured, the pendant 105 may have the ability to harvest, record, analyze, and transmit at least one channel of ECG data.

In another embodiment, the pendant 105 may require replaceable battery packs to ensure continued monitoring with limited interruption. For example, and without limitation, the battery may be sized to ensure seven-day operation between charges and may have a charge life of 200 cycles minimum. Also for example, and without limitation, the battery pack may include all necessary charging circuitry and may be configured to electrically connect to the USB charger using the mini-USB. When installed in the pendant 105, the charging connector may be protected from water ingress such that the pendant 105 may meet ingress protection (IP) requirements.

The carrier component of the physiological signal monitoring system may comprise one of a potential multitude of carriers. Such carriers may vary both in structure and in function, dependent on the physiological parameters to be measured. For example, and without limitation, each carrier may have a common connection point, or similar mechanical and/or electrical attachment structure, that may advantageously allow for simple and easy connection of any physically and/or electrically compatible accessory to the pendant 105 component. For example, and without limitation, both the pendant 105 and the carrier may comprise a standard external zero-insertion contact surface. The respective contact surfaces of the pendant 105 and the carrier may support electrical communication between these two components.

Figure 4A:
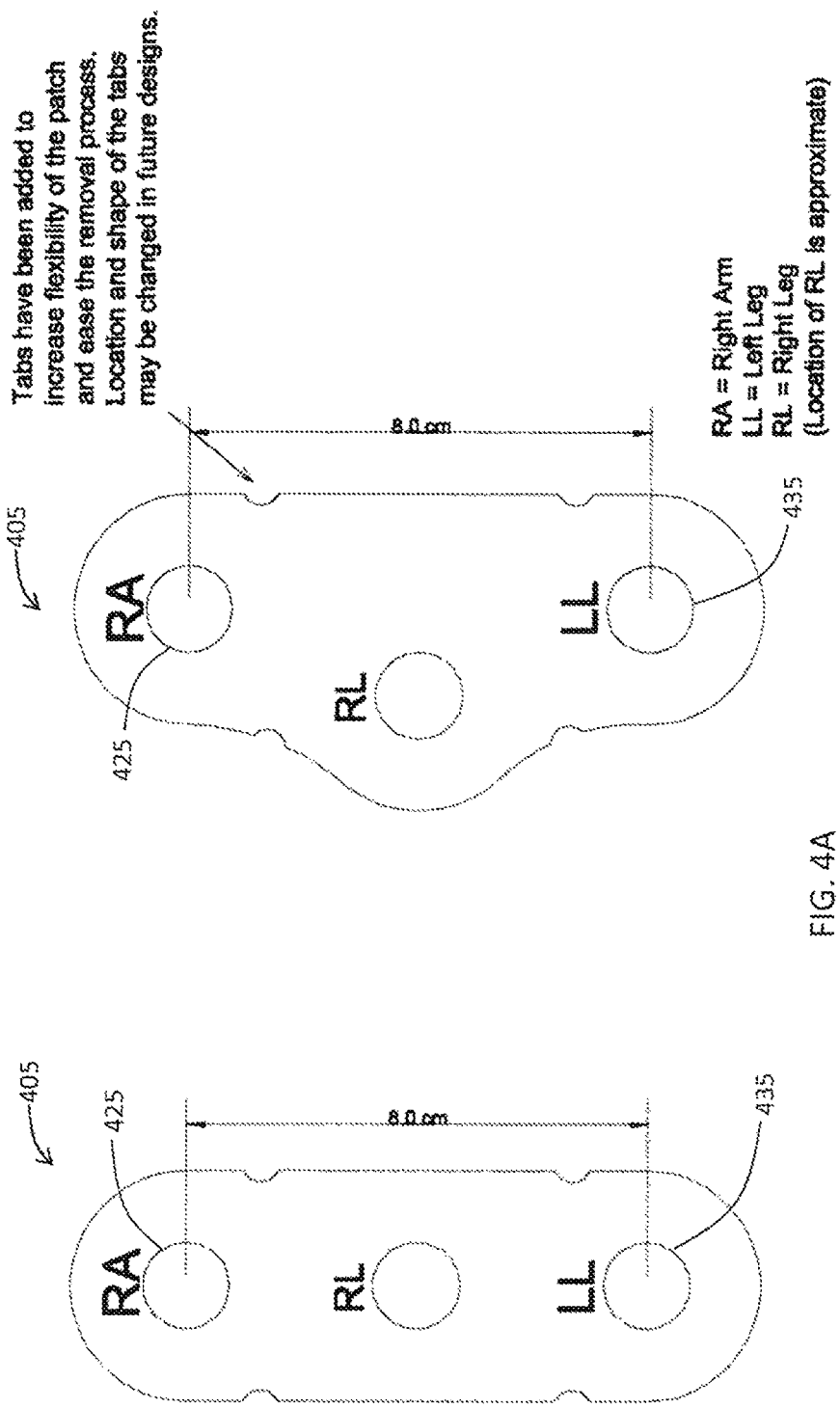
FIG. 4A is a front elevation and schematic view of two exemplary single channel patch components of a pendant physiological signal monitor according to an embodiment of the present invention.
Figure 4B:
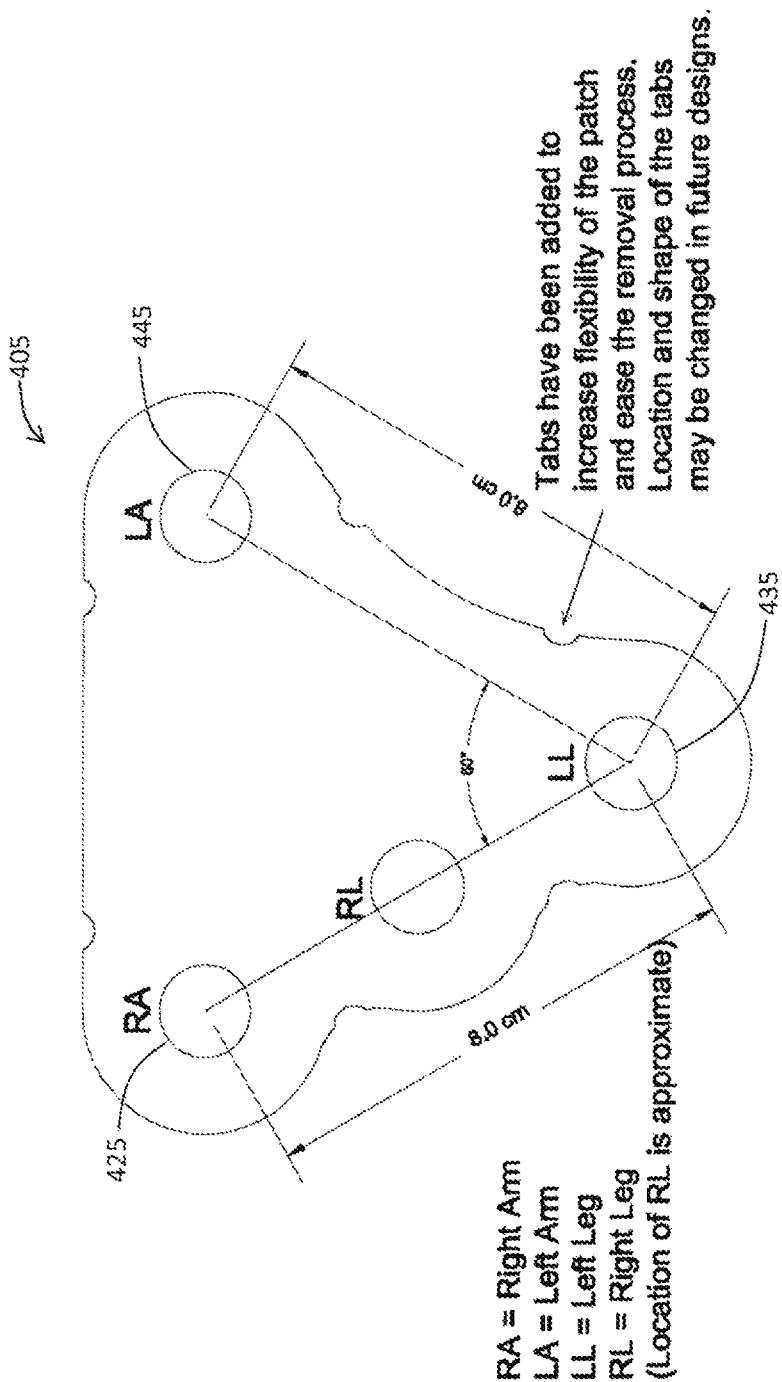
FIG. 4B is a front elevation and schematic view of an exemplary two channel patch component of a pendant physiological signal monitor according to an embodiment of the present invention.
Figure 5A:
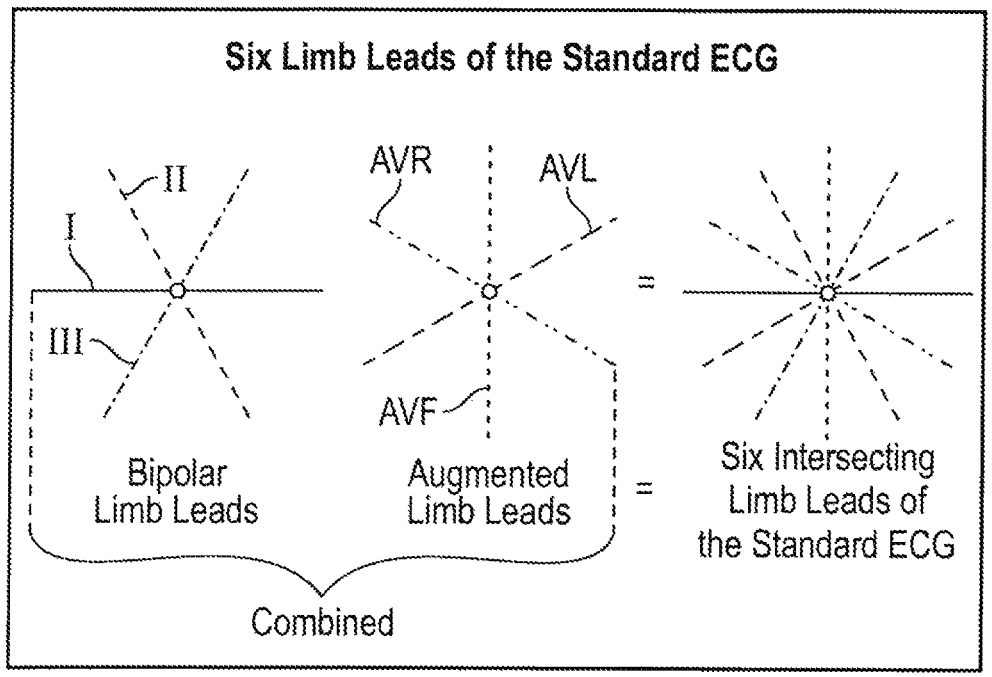
FIG. 5A is a graph illustrating limb leads of a standard ECG known in the art.
Figure 5B:
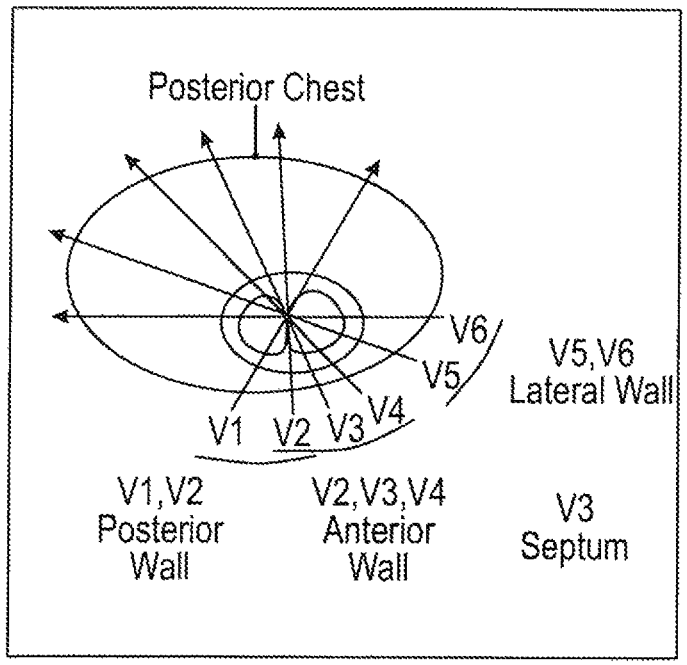
FIG. 5B is a graph illustrating chest leads of a standard ECG known in the art.
Figure 5C:
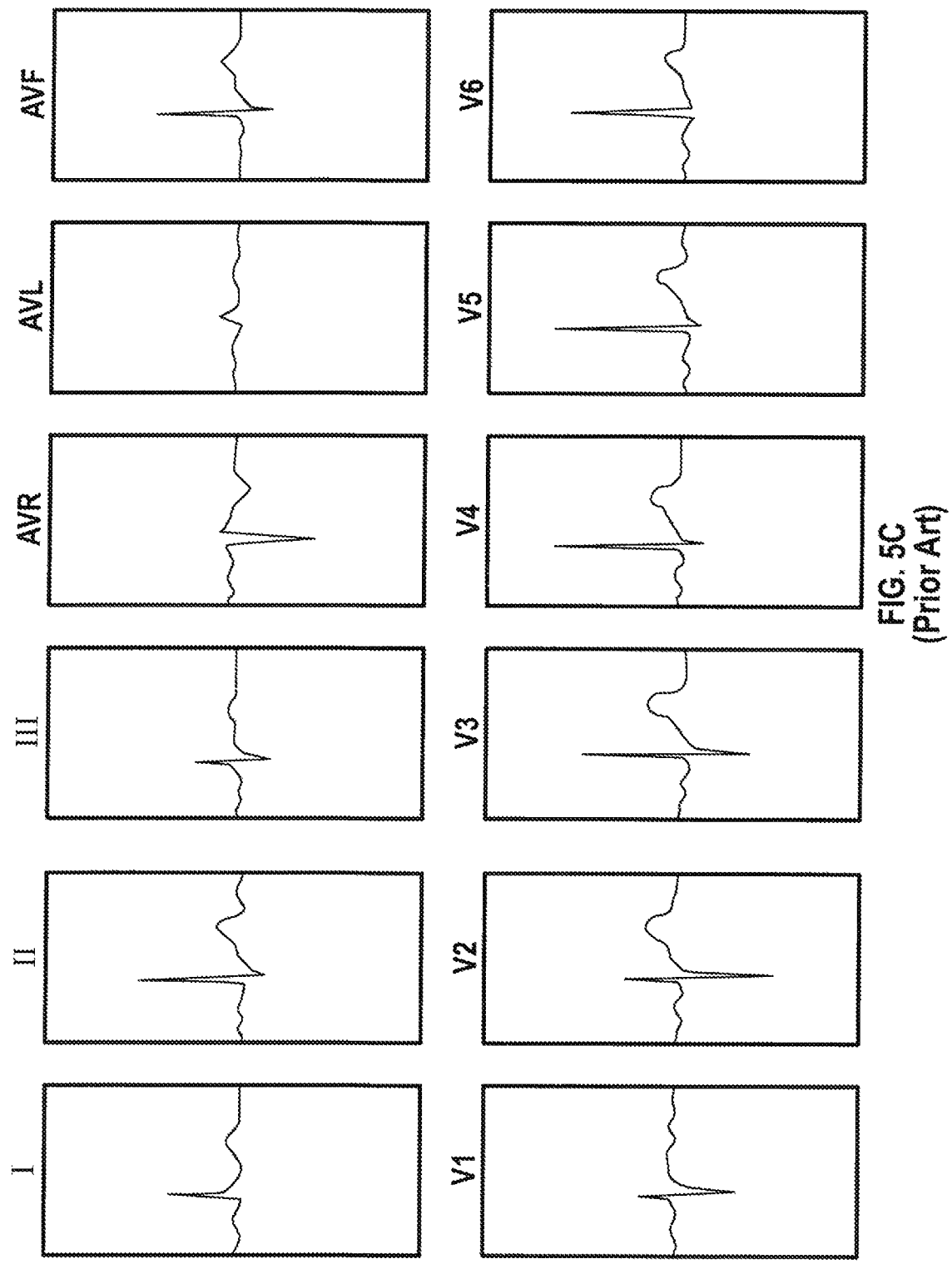
FIG. 5C is a graph illustrating exemplary ECG output of the limb leads of FIG. 5A and the chest leads of FIG. 5B, as known in the art.

Referring now to FIGS. 4A and 4B, and continuing to refer to FIGS. 1 and 3, the carrier component may comprise a flexible patch 405 which may include some method of mechanical location and interlock to the pendant 105. For example, and without limitation, the carrier component as implemented as the flexile patch 405 may comprise some combination of a flexible printed circuit board (PCB) and a fabric overlay configured to advantageously facilitate user comfort when placed in contact with the user's skin. For example, and without limitation, the flexile patch 405 may comprise a patch style ECG recorder. The ECG recorder may support both single channel (FIG. 4A) and double channel (FIG. 4B) procedures, and described in more detail below. The patch 405 may advantageously be wearable for seven (7) days without causing skin irritation and may conform to the patient's contours. The patch 405 may feature water resistance during patient showering to advantageously support the seven-day wear time. For example, and without limitation, the patch 405 may support a pendant 105 weight of up to 36 grams.

For example, and without limitation, the flexile patch 405 may be designed as one of a Single Channel Patch (see FIG. 4A) and a Two Channel Patch (see FIG. 4B). As illustrated at FIG. 4A, the single channel patch 405 may support right arm RA and left leg LL with an approximate distance between electrodes of 8 centimeters (CM), which may advantageously allow capture of a clean signal with enough amplitude of the electrical movement. The single channel patch 405 may also support a third electrode that may be used as Right Leg RL drive or reference electrode. As illustrated at FIG. 4B, the two channel patch 405 may support right arm RA, left leg LL, right leg RL, left arm LA and a reference electrode. The spacing for standard ECG lead II (right arm RA and left leg LL) may be 8 CM at its approximate distance. The second ECG channel (right leg RL, left arm LA, and reference electrode) may be between 4 CM and 8 CM apart. For example, and without limitation, these requirements may advantageously be supported using four electrodes, with the fourth electrode being interchangeable for the Right Leg drive and reference electrode.

Thoughtful selection of electrode diameter may advantageously provide a signal to noise ratio needed for clean ECG while still adhering to the body for seven days. For example, and without limitation, standard electrodes may be characterized by a diameter of approximately 1.5 CM. A carrier component 405 may be configured such that at least 1 CM of margin may be maintained between an edge of the patch 405 to a perimeter of the electrode to advantageously ensure a secure contact of the electrodes to the patient's skin. To advantageously facilitate ease of placement of a double channel patch 405, the top of the patch may be shaped as a straight side while the remaining sides may have curved edges to reduce as much as possible the adhesive contact.

Figure 6:
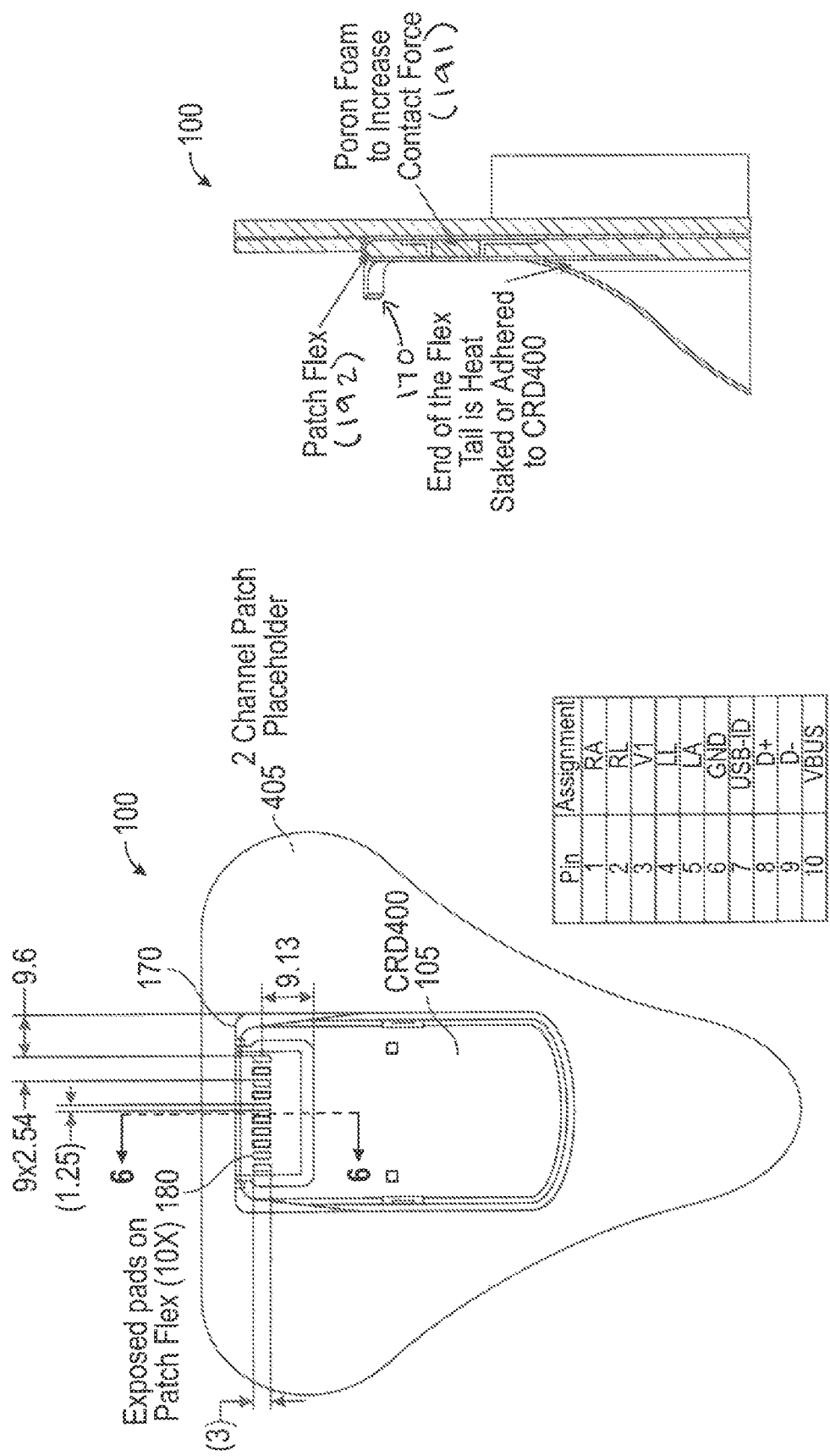
FIG. 6 is a front elevation view and a side elevation cutaway view of an assembled pendant physiological signal monitor according to an embodiment of the present invention.
Figure 7:
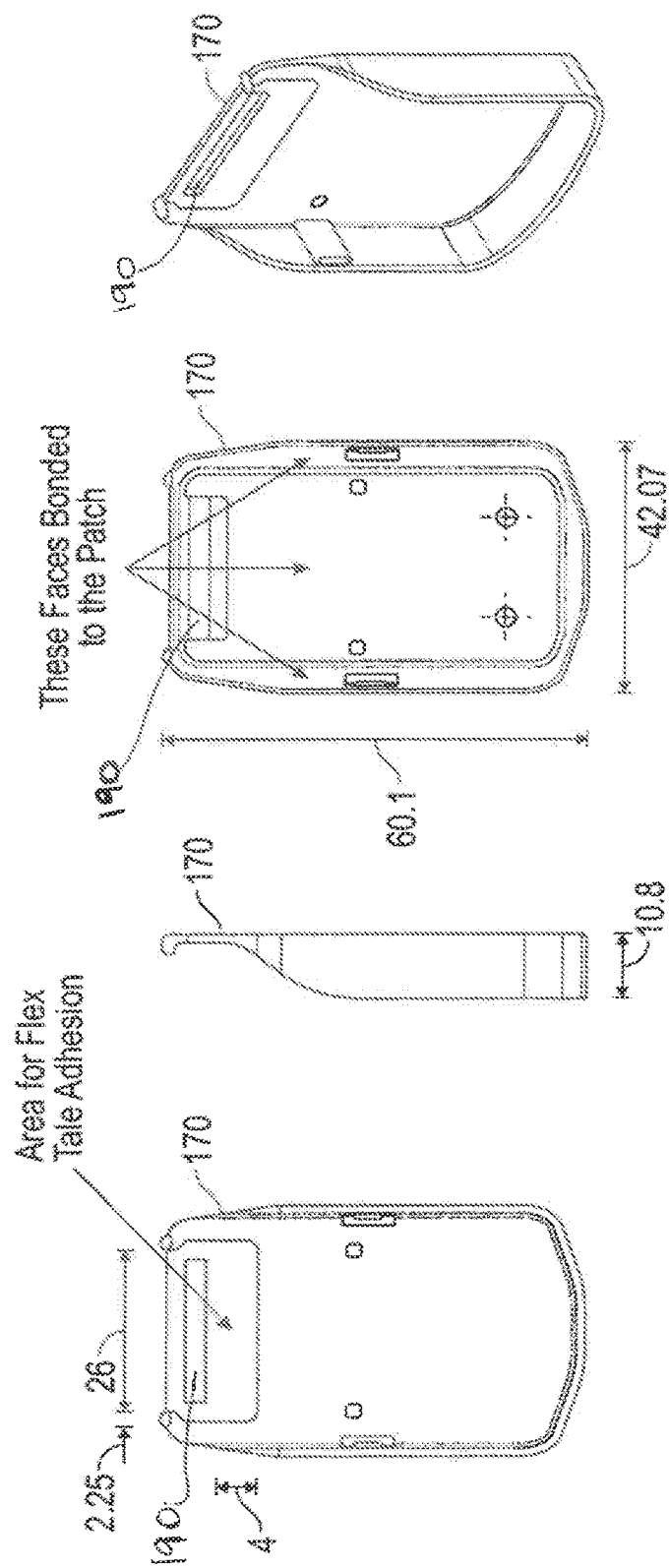
FIG. 7 is a front elevation view, side elevation view, rear elevation view, perspective view and schematic view of an exemplary cradle of a carrier component as implemented in a pendant physiological signal monitor according to an embodiment of the present invention.

The flexible patch 405 may provide electrical connection to some number of electrodes that may be coated in an electrically-conductive material (e.g., gold, Silver-Silver Chloride) and may be configured to electrically interconnect to the pendant 105 via hard gold pads 180. For example, and without limitation, electrical connectivity of the ECG electrodes to the carrier component may be through pogo or small cantilever beam contacts that may be soldered to an interface board and configured in electrical contact with the gold pads 180 on the pendant 105 when installed. Also for example, and without limitation, one or more ECG electrodes may be secured to the patient's chest using adhesives applicable for the situation. An adhesive may be employed based on an ability to advantageously hold the total device 100 weight (e.g., up to 50 g) during a long-term wear period (defined as up to seven days). For example, and without limitation, the adhesive may comprise a non-woven material, the application of which may extend a few millimeters beyond the contour of the patch 405 in order to advantageously hold the patch pendant weight for a longer period of time without de-adhering from the patient's skin. Referring additionally to FIGS. 6 and 7, the pendant 105 may be configured to removably attach to a cradle 170 that may be mounted on the patch 405. For example, and without limitation, the cradle 170 may be fully contained within a perimeter of the patch 405. As depicted in FIG. 7, the cradle may contain an aperture 190. A foam structure 191 may be carried by the aperture 190, as depicted in FIG. 6. Also, as shown in FIG. 6, the flexible printed circuit board 192 may occlude the aperture 190 on the first side of the cradle 170, extend over the top edge of the cradle, and down over the aperture 190 to occlude the aperture 190 on the second side of the cradle 170, securing the foam structure 191 within the aperture 190 between the two portions of flexible printed circuit board 192. Positioning the foam insert 191 between two portions of the flexible printed circuit board 192 as shown in FIG. 6, may increase the contact force of the second electrical connector of the flexible printed circuit board and the electrical connector of the housing 107.

As described above, each carrier 405 may comprise of a varying number and type of physiological signal harvesting means (for example, and without limitation, patch-type body electrodes, cable-type electrodes 140, hidden fingertip electrodes 150, accelerometers, strain gauges). Also for example, and without limitation, a carrier may support some variation and/or combination of the following harvesting applications:

Electrocardiogram (ECG)
Electromyogram (EMG)
Electroencephalogram (EEG)
Body Temperature
Heart Rate
Pedometer
Blood Pressure
Pulse Oximetry
Respiratory Rate
Posture/Body Orientation
Sleep Monitoring The list above is by no means comprehensive, as a person skilled in the art will recognize that the technology disclosed herein may be applied to measure any mechanically-detectable physiological parameter.

In one embodiment of the physiological signal monitoring system 100, the pendant 105 and the carrier 405 may be configured to operate in combination to measure and/or evaluate some number of input channels and/or leads in each application where such multi-channel inputs may be desired (for example, and without limitation, 1, 2, . . . , N-lead ECG). A system 100 may be configured with accessory components that may provide the option of monitoring multiple parameters simultaneously. The available components for use in each monitoring application listed above may differ in both the number of channels supplied and the harvest means in terms of both hardware and/or relative anatomical orientation.

Also for example, and without limitation, one available carrier may provide the ability of the pendant 105 to record and analyze three (3) channels of ECG data in a variety of different combinations of medically acceptable lead orientations (V1, V2, etc.). Another carrier may only monitor any one medically acceptable channel of ECG data. The means of signal harvesting may be determined by the selected carrier, which may consist of any number of standard cables, patch-type electrodes, or some combination of both (for example, and without limitation, 3-wire cable, 5-wire cable, or other industry-standard cable configuration). The carrier may also comprise a retractable system wherein one cable type electrode may be withdrawn from a parent casing.

In another embodiment of the physiological signal monitoring system, a microphone that may be built in either the pendant 105 or the selected carrier, wherein the wearer may be able to initiate an audio recording. The physiological signal monitoring system may be configured to save the audio information recorded, which may either be a preset duration for each initiation sequence, or a length of recording determined by the user through means of prolonged press of the recording activation button 160 or, alternatively, of an initiation sequence upon system startup.

For example, and without limitation, the physiological signal monitoring system may be carried or worn by a patient through means of adhesion, garment attachment, and/or through an integrated wristband, necklace, or similar accessory. The means and nature of device-to-patient attachment may be dependent upon the intended use and the type of carrier utilized. The entire system may be constructed in such a way as to be water/sweat-resistant.

For example, and without limitation, the physiological signal monitoring system may be made available in either a medically-prescribed form or as an over-the counter (OTC) device. In the prescribed form, the physiological signal monitoring system may use one or more of its communication means mentioned early to send the acquired data to a monitoring center. For example, and without limitation, the monitoring center may feature human over read, or no human over read (e.g., fully automated monitoring). For example, and without limitation, the monitoring center may analyze and process the data through a proprietary software system and process, and reports may be generated and sent to a physician, or the data may be sent directly to the physician in raw form and/or as an automatically configured report. The information may also be transmitted to a mobile device application which may be downloaded by a user onto her own instance of the physiological signal monitoring system. For example, and without limitation, the mobile device application or cellular network hardware on the patch may be able to send data over data networks (see App-Based Carrier and Data-Routing disclosure below) to the appropriate monitoring center, physician, or other downstream user, and may eliminate the need for the patient to carry any mobile device or a second mobile device in addition to her own.

In another embodiment, the physiological signal monitoring system may employ its means of communication to advantageously display acquired information to a user with a recreational purpose. For example, and without limitation, an interface may be provided by a computer program or mobile device application, for which the physiological signal monitoring system may be configured to recognize a user's selected interfacing means and may transmit the acquired physiological data according to the interface detected. The software program/application may be configured to read data sent to it by the physiological signal monitoring system and display those data to the user in such a way that it is meaningful and easy to understand. This application may generally have advantageous uses in the realm of individual health and fitness. The interfacing program/application may also be configured to advantageously generate warnings and reports to inform the user of any potential health problems detected by the physiological signal monitoring system. All versions of the interface may be capable of providing different customizable reports of both physiological events and trending.

App-Based Carrier and Data-Routing

The physiological signal monitoring system described herein may further consist of a software application developed for use primarily in mobile device users requiring or desiring access to a data source (for example, and without limitation, mobile service providers such as Sprint, AT&T, T-Mobile, and their competitors). Current plans and services that allow access to data networks limit user choices regarding carriers. Such plans and services also carry risks for expensive overage charges, and the only existing alternative requires using specialized SIM cards or 3rd party companies.

The mobile application described herein may act as and/or may utilize a private Access Point Name (APN), wherein the user may be able to circumvent standard data rate charges from his/her mobile service provider for both non-specific and/or specific services necessitating access to a mobile network. The provider of the application may pay a fixed fee to be charged at the time of any connection to the data server of any given mobile service provider to be chosen by the application provider. Any data usage subsequent to the initial connection may then be handled by the provider of the application, and rates to be charged to the application provider by the service provider may then be negotiated between those two respective parties. The present invention may advantageously eliminate risk of overage charges, 3rd parties, and expensive plans, and may allow desiring individuals or entities to provide their own data access/servers while only paying a relatively small fee for access to large mobile network companies for each connection to the mobile network itself.

In one embodiment, the application may serve as a means to allow for the application provider to negotiate an agreement with the mobile service/data provider to allow the device utilizing the application to connect to the mobile service's data network at a flat rate. In such a fee-for-service arrangement, a fee may be charged for each connection and the total data usage may be pre-set and paid for by the application provider to the mobile service provider. For example, and without limitation, this application may need to provide a Network Identifier within the APN, and may also potentially require an Operator Identifier depending on the configuration of the application and the agreement between the application provider and the service provider. This application may eliminate the necessity of a specialized SIM card to access an alternate data network.

The mobile application may be used in any field that would benefit from the ability to advantageously provide consumers with data network access either for free or for a flat rate while eliminating the risk for overage charges. For example, and without limitation, mobile device games requiring data access (especially larger amounts), mobile apps that transfer large amounts of data over a network (modem telemedical devices), and a variety of other areas like video chatting and internet browsing may make advantageous use of the mobile application.

For example, and without limitation, mobile device users typically have capitalized data plans with set volumes and costs. Such a user may find it difficult to estimate if a desired download or use of a mobile application will exceed her remaining available data plan that, in turn, may decrease the user's desire to purchase the app for fear of incurring additional data charges. The mobile application described herein may allow application developers to market their mobile applications to include prepaid data allowances, which may or may not be scheduled to expire, to cover the data usage of the mobile application. The application providers, developers, and/or cellular data companies may promote more use of the application (and data) by offering capped data rates or reasonable overage charges that may be agreed upon prior to usage. For example, and without limitation, the application provider may negotiate and pre-purchase bulk data from mobile service providers (such as users listed above or from Mobile Broadcast/Multicast Network Operator providers) and may provide this data to their users in variable amounts based on actual usage. For example, and without limitation, such usage may comprise actual data usage, unlimited data usage, or fixed amount usage based on a flat fee. The application provider may price the application and/or rates based on the package or product or amount of data offered. The application described herein may offer variable pricing options based on the consumers desired requirements, such as number of ECG strips to be analyzed or total amount of time the monitoring device is worn. For example, and without limitation, the application may also work in other consumer environments characterized by data usage, such as movie downloads, music streaming, mobile apps for children, and gaming just to name a few.

Figure 8:
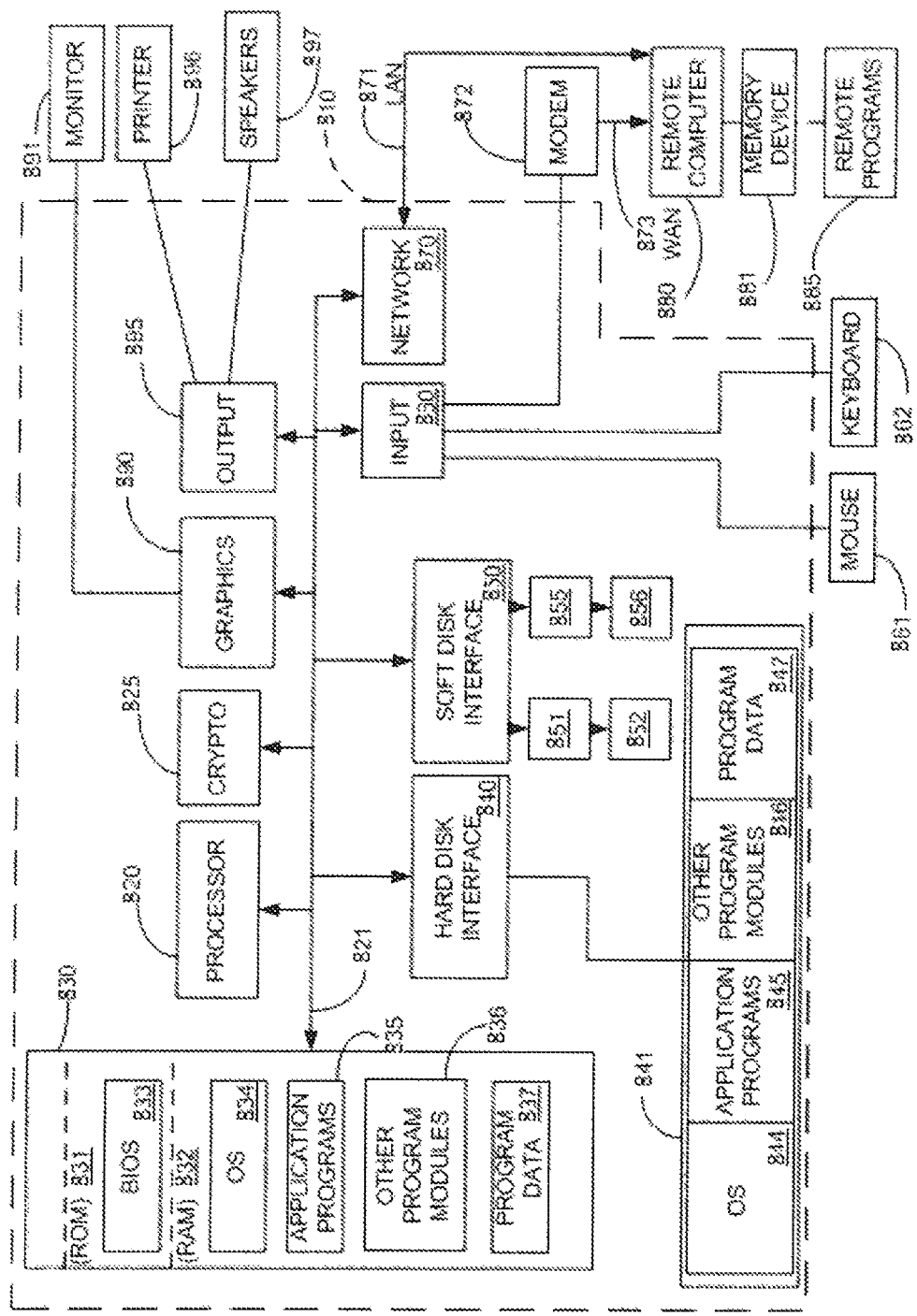
FIG. 8 is a block diagram representation of a machine in the example form of a computer system according to an embodiment of the present invention.
Figure 9:
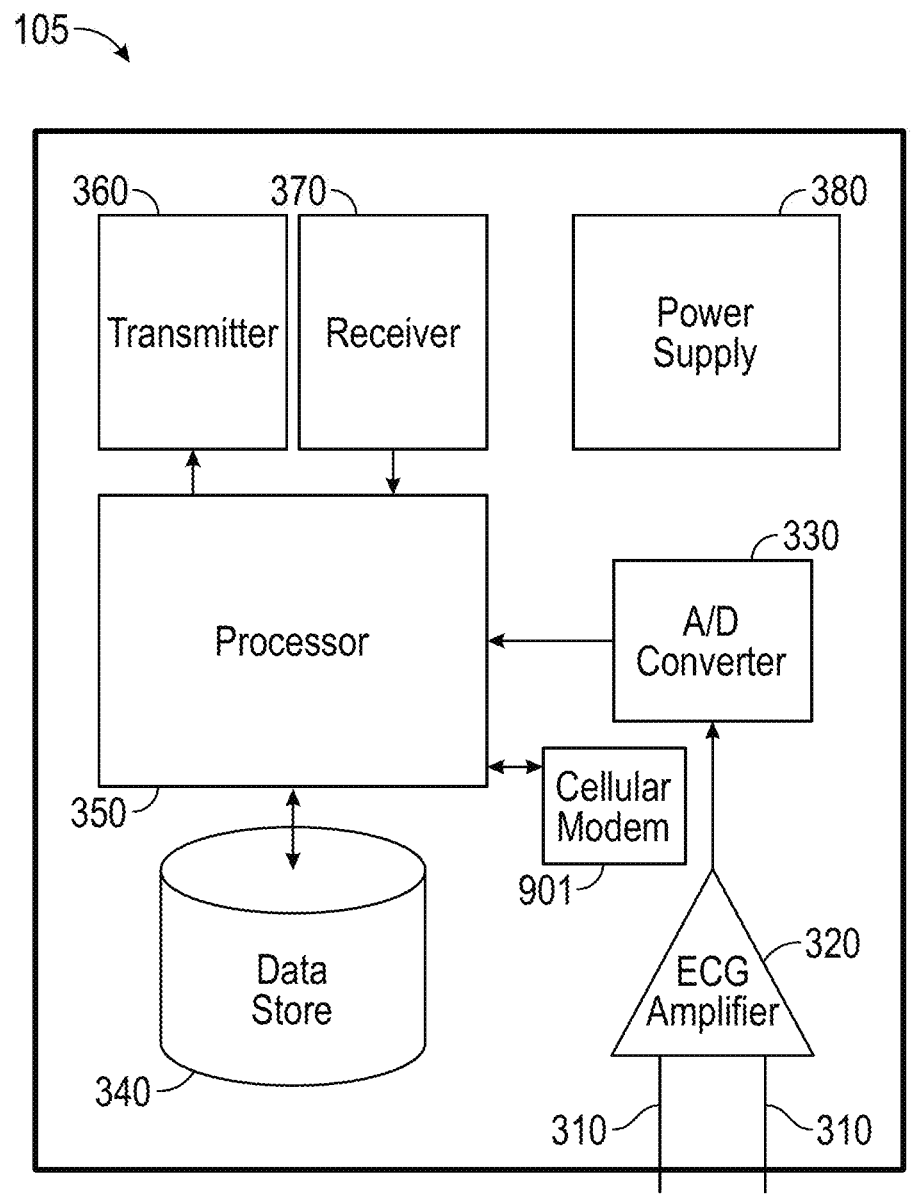
FIG. 9 is a schematic block diagram of electronics in a pendant component of pendant physiological signal monitor according to an embodiment of the present invention.

A skilled artisan will note that one or more of the aspects of the present invention may be performed on a computing device. The skilled artisan will also note that a computing device may be understood to be any device having a processor, memory unit, input, and output. This may include, but is not intended to be limited to, cellular phones, smart phones, tablet computers, laptop computers, desktop computers, personal digital assistants, etc. FIG. 8 illustrates a model computing device in the form of a computer 810, which is capable of performing one or more computer-implemented steps in practicing the method aspects of the present invention. Components of the computer 810 may include, but are not limited to, a processing unit 820, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI).

The computer 810 may also include a cryptographic unit 825. Briefly, the cryptographic unit 825 has a calculation function that may be used to verify digital signatures, calculate hashes, digitally sign hash values, and encrypt or decrypt data. The cryptographic unit 825 may also have a protected memory for storing keys and other secret data. In other embodiments, the functions of the cryptographic unit may be instantiated in software and run via the operating system.

A computer 810 typically includes a variety of computer readable media. Computer readable media can be any available media that can be accessed by a computer 810 and includes both volatile and nonvolatile media, removable and non-removable media. By way of example, and not limitation, computer readable media may include computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer 810. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer readable media.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 8 illustrates an operating system (OS) 834, application programs 835, other program modules 836, and program data 837.

The computer 810 may also include other removable/non-removable, volatile/nonvolatile computer storage media. By way of example only, FIG. 8 illustrates a hard disk drive 841 that reads from or writes to non-removable, nonvolatile magnetic media, a magnetic disk drive 851 that reads from or writes to a removable, nonvolatile magnetic disk 852, and an optical disk drive 855 that reads from or writes to a removable, nonvolatile optical disk 856 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 841 is typically connected to the system bus 821 through a non-removable memory interface such as interface 840, and magnetic disk drive 851 and optical disk drive 855 are typically connected to the system bus 821 by a removable memory interface, such as interface 850.

The drives, and their associated computer storage media discussed above and illustrated in FIG. 8, provide storage of computer readable instructions, data structures, program modules and other data for the computer 810. In FIG. 8, for example, hard disk drive 841 is illustrated as storing an OS 844, application programs 845, other program modules 846, and program data 847. Note that these components can either be the same as or different from OS 833, application programs 833, other program modules 836, and program data 837. The OS 844, application programs 845, other program modules 846, and program data 847 are given different numbers here to illustrate that, at a minimum, they may be different copies. A user may enter commands and information into the computer 810 through input devices such as a keyboard 862 and cursor control device 861, commonly referred to as a mouse, trackball or touch pad. Other input devices (not shown) may include a microphone, joystick, game pad, satellite dish, scanner, touch screen, voice entry, or the like. For example, and without limitation, these and other input devices may be connected to the processing unit 820 through a user input interface 860 that is coupled to the system bus, and/or may be connected by other interface and bus structures, such as a High-Definition Multimedia Interface (HDMI), parallel port, game port or a universal serial bus (USB). A monitor 891 or other type of display device is also connected to the system bus 821 via an interface, such as a graphics controller 890. In addition to the monitor, computers may also include other peripheral output devices such as speakers 897 and printer 896, which may be connected through an output peripheral interface 895.

The computer 810 may operate in a networked environment using logical connections to one or more remote computers, such as a remote computer 880. The remote computer 880 may be a personal computer, a server, a router, a network PC, a peer device or other common network node, and typically includes many or all of the elements described above relative to the computer 810. Although only a memory storage device 881 has been illustrated in FIG. 8, the networked environment may be configured to support distributed storage resources (e.g., cloud storage). The logical connections depicted in FIG. 8 include a local area network (LAN) 871 and a wide area network (WAN) 873, but may also include other networks 140. Such networking environments are commonplace in offices, enterprise-wide computer networks, intranets and the Internet.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. The modem 872, which may be internal or external, may be connected to the system bus 821 via the user input interface 860, or other appropriate mechanism. In a networked environment, program modules depicted relative to the computer 810, or portions thereof, may be stored in the remote memory storage device. By way of example, and not limitation, FIG. 8 illustrates remote application programs 885 as residing on memory device 881.

The communications connections 870 and 872 allow the device to communicate with other devices. The communications connections 870 and 872 are an example of communication media. The communication media typically embodies computer readable instructions, data structures, program modules or other data in a modulated data signal such as a carrier wave or other transport mechanism and includes any information delivery media. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

Integrated Communications

In some embodiments, no additional mobile device may be necessary to communicate on a data network. In such an embodiment, the pendant 105 may include a cellular modem 901 enabling communication on a data network, which may be a cellular network. The inclusion of cellular modem 901 within the pendant 105 may eliminate the need for the pendant 105 to communicate with a mobile device. However, the communication with a cellular device may be beneficial to maintain in some embodiments incorporating the cellular modem 901. In an embodiment including a cellular modem 901, one or more features otherwise found in the mobile device may be incorporated into the pendant 105.

A skilled artisan will note that the previously described computing device may be housed within the pendant 105. One or more components of the computing device may be shared with components of the pendant 105 when the computing device is located in the pendant 105. In such an embodiment, the cellular modem 901 may be in wired or wireless electrical communication with one or more components comprising the SoC 110. The cellular modem 901 may be located within the same housing as the SoC 110.

The pendant 105 may include a voice recorder. The voice recorder may be activated by an recording activation button 160, switch, toggle, or the like. In some embodiments, the voice recorder may be activated by detection of one or more spoken commands. The voice recorder may be adapted to record ambient noise when activated. The recording captured by the voice recorder may be paired with ECG data from a corresponding time. The patient may use the voice recorder to record symptoms, observations, or the like at the time the voice recorder is activated. In this way, an individual reviewing the voice recorder data and the ECG data may determine what a patient experiences during particular heart activity.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A physiological signal monitoring system comprising: a pendant comprising: a housing, an electrical connector located on a first side of the housing, a processor in electrical communication with the electrical connector and carried within the housing, and a data store in electrical communication with the processor and carried within the housing; a patch having a perimeter, comprising: a plurality of electrodes carried within the perimeter of the patch, and a flexible printed circuit board having an electrical connector in communication with each of the plurality of electrodes, wherein the electrical connector includes a plurality of exposed pads, a cradle having a perimeter fully contained within the perimeter of the patch, a first side secured to the patch, a second, opposing side, and an aperture formed through an entirety of a thickness of the cradle from the first side to the second side, wherein the flexible printed circuit board fully occludes the aperture on the first side, extends over an edge of the cradle, and over the aperture on the second side to fully occlude the aperture on the second side, securing a foam insert within the aperture, wherein the foam is configured to increase a contact force; and a non-woven adhesive material extending over an entirety of an area of a backside of the patch and beyond the perimeter of the patch and adapted to support a total device weight; wherein a combined weight of the pendant, the non-woven adhesive material, the cradle, and the patch define the total device weight; wherein the electrical connector of the flexible printed circuit board is positioned on the second side of the cradle to provide an electrical connection to the electrical connector of the pendant when the pendant is carried by the cradle with the first side of the pendant proximate the second side of the cradle; wherein the pendant is configured to removably couple with the cradle of the patch and be fully contained within the perimeter of the cradle of the patch; and wherein the processor is configured to receive, from at least one of the plurality of electrodes, electrical signals from a heart of a patient, and to store the electrical signals as electrocardiogram (ECG) data to the data store.

2. The physiological signal monitoring system according to claim 1, wherein the pendant further comprises a cellular modem.

3. The physiological signal monitoring system according to claim 1, wherein the pendant further comprises a recording activation button.

4. The physiological signal monitoring system according to claim 1, wherein the plurality of electrodes of the patch further comprises a first electrode and a second electrode, defined as an RA electrode and an LL electrode, respectively, which are configured to detect the electrical signals; wherein the RA electrode and the LL electrode are positioned at least 8.0 centimeters (cm) apart.

5. The physiological signal monitoring system according to claim 4, wherein the plurality of electrodes of the patch further comprises a third electrode, defined as an LA electrode, which is configured to detect the electrical signals; wherein the LA electrode and the LL electrode are positioned at least 8.0 cm apart.

6. The physiological signal monitoring system according to claim 1, wherein the housing further comprises a plurality of integrated electrodes configured to detect the electrical signals.

7. The physiological signal monitoring system according to claim 1, wherein the pendant comprises at least one device interface each configured to receive signal communication from at least one removable auxiliary component.

8. The physiological signal monitoring system according to claim 7, wherein the at least one removable auxiliary component is selected from the group consisting of a cable harness, a retractable monitor device, and a finger electrode adapter.

9. The physiological signal monitoring system according to claim 7, wherein the processor of the pendant is further configured to receive from the at least one removable auxiliary component a physiological input of a type selected from the group consisting of electromyogram (EMG), electroencephalogram (EEG), body temperature, heart rate, pedometer, blood pressure, pulse oximetry, respiratory rate, posture/body orientation, and sleep monitoring.

10. The physiological signal monitoring system according to claim 9, wherein the pendant comprises a recording activation button configured to initiate receipt of at least one of the electrical signals and the physiological input by the processor.

11. The physiological signal monitoring system according to claim 1, wherein the pendant weighs up to 36 grams.

12. A physiological signal monitoring system comprising: a pendant comprising: a housing, an electrical connector located on a first side of the housing, a processor in electrical communication with the electrical connector and carried within the housing, a data store in electrical communication with the processor and carried within the housing, and a cellular modem; a patch having a perimeter, comprising: a plurality of electrodes carried within the perimeter of the patch, and a flexible printed circuit board having an electrical connector in communication with each of the plurality of electrodes, wherein the electrical connector includes a plurality of exposed pads; a cradle having a perimeter fully contained within the perimeter of the patch, a first side secured to the patch, a second, opposing side, and an aperture formed through an entirety of a thickness of the cradle from the first side to the second side, wherein the flexible printed circuit board fully occludes the aperture on the first side, extends over an edge of the cradle, and over the aperture on the second side to fully occlude the aperture on the second side, securing a foam insert within the aperture, wherein the foam is configured to increase a contact force; and a non-woven adhesive material extending over an entirety of an area of a backside of the patch and beyond the perimeter of the patch and adapted to support a total device weight; wherein a combined weight of the pendant, the non-woven adhesive material, the cradle and the patch define the total device weight; wherein the electrical connector of the flexible printed circuit board is positioned on the second side of the cradle to provide an electrical connection to the electrical connector of the pendant when the pendant is carried by the cradle with the first side of the pendant proximate the second side of the cradle; wherein the pendant is configured to removably couple with the cradle of the patch and be fully contained within the perimeter of the cradle of the patch; and wherein the processor is configured to receive, from at least one of the plurality of electrodes, electrical signals from a heart of a patient, and to operate the cellular modem to transmit the electrical signals as electrocardiogram (ECG) data to a cellular network.

13. The physiological signal monitoring system according to claim 12, wherein the cellular modem further comprises an integrated antenna configured to transmit the electrical signals wirelessly.

14. The physiological signal monitoring system according to claim 12, wherein the plurality of electrodes of the patch further comprises a first electrode and a second electrode, defined as an RA electrode and an LL electrode, respectively, which are configured to detect the electrical signals; wherein the RA electrode and the LL electrode are positioned at least 8.0 centimeters (cm) apart.

15. The physiological signal monitoring system according to claim 14, wherein the plurality of electrodes of the patch further comprises a third electrode, defined as an LA electrode, which is configured to detect the electrical signals; wherein the LA electrode and the LL electrode are positioned at least 8.0 cm apart.

16. The physiological signal monitoring system according to claim 12, wherein the pendant comprises at least one device interface each configured to receive signal communication from at least one removable auxiliary component.

17. The physiological signal monitoring system according to claim 16, wherein the processor of the pendant is further configured to receive from the at least one removable auxiliary component a physiological input of a type selected from the group consisting of electromyogram (EMG), electroencephalogram (EEG), body temperature, heart rate, pedometer, blood pressure, pulse oximetry, respiratory rate, posture/body orientation, and sleep monitoring; and wherein the processor is configured to operate the transmitter to transmit the physiological input to at least one of the cellular network access point and a base station.

18. A method of monitoring physiological events generated as electrical signals, the method comprising: providing a pendant that includes a housing, an electrical connector located on a first side of the housing, a processor in electrical communication with the electrical connector and carried within the housing, a data store in electrical communication with the processor and carried within the housing, and a cellular modem; providing a patch having a perimeter that includes a plurality of electrodes carried within the perimeter of the patch and a flexible printed circuit board having an electrical connector in communication with each of the plurality of electrodes, wherein the electrical connector includes a plurality of exposed pads; providing a cradle that includes a perimeter fully contained within the perimeter of the patch, a first side secured to the patch, a second, opposing side, and an aperture formed through an entirety of a thickness of the cradle from the first side to the second side, wherein the flexible printed circuit board fully occludes the aperture on the first side, extends over an edge of the cradle, and over the aperture on the second side to fully occlude the aperture on the second side, securing a foam insert within the aperture, wherein the foam is configured to increase a contact force; and wherein the electrical connector of the flexible printed circuit board is positioned on the second side of the cradle; providing a non-woven adhesive material extending over an entirety of an area of a backside of the patch and beyond the perimeter of the patch and adapted to support a total device weight; determining, using the processor, that the pendant is removably coupled to the cradle of the patch; operating the processor of the pendant to receive the electrical signals from the plurality of electrodes of the patch; electrically connecting at least one removable auxiliary component to the pendant; receiving from the at least one removable auxiliary component a physiological input of a type selected from the group consisting of electromyogram (EMG), electroencephalogram (EEG), body temperature, heart rate, pedometer, blood pressure, pulse oximetry, respiratory rate, posture/body orientation, and sleep monitoring; and operating the cellular modem of the pendant to transmit the physiological input to at least one of a cellular network access point and a base station.

19. The method according to claim 18, further comprising storing electrocardiogram (ECG) data in the data store that represents the electrical signals received from the patch.

* * * * *